Figure 1:
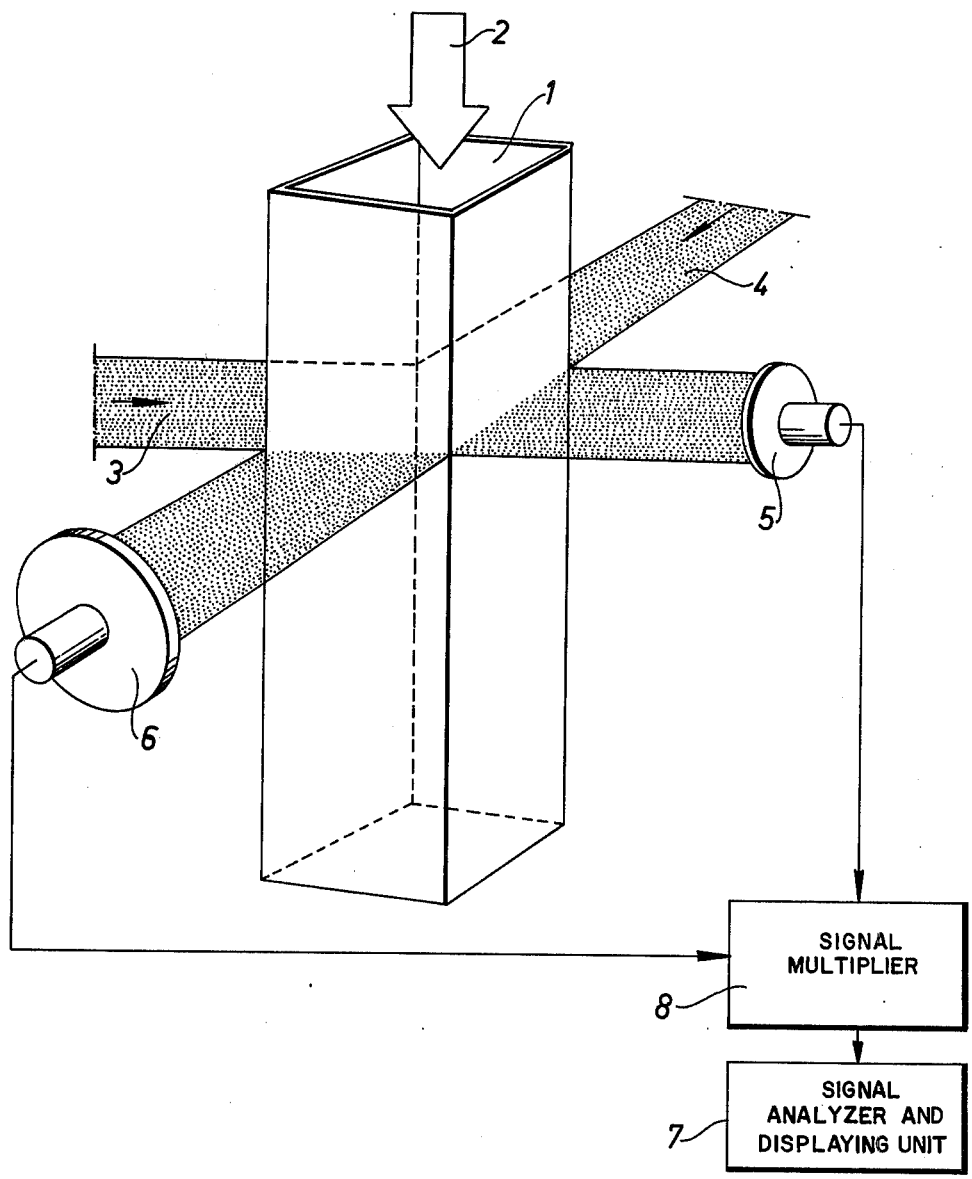

United States Patent [19]

Hill

[11] 4,037,966
[45] July 26, 1977

[54] METHOD AND DEVICE FOR EXAMINING PULP FOR THE PRESENCE OF SHIVES

[75] Inventor: Jan Hill, Taby, Sweden

[73] Assignee: AB Tellusond, Stockholm, Sweden

[21] Appl. No.: 685,924

[22] Filed: May 12, 1976

[30] Foreign Application Priority Data

May 14, 1975   Sweden .............................. 7505539

[51] Int. Cl.² ............................................ G01N 21/26
[52] U.S. Cl. ............................ 356/102; 250/222 PC;
250/345; 250/575; 356/51; 356/201
[58] Field of Search ................. 356/51, 201, 208, 102;
250/222 PC, 343, 345, 573, 575

[56] References Cited

U.S. PATENT DOCUMENTS

| 3,028,501 | 4/1962 | Lamparter ..................... 250/222 PC |
| 3,153,727 | 10/1964 | Nathan .............................. 356/102 |
| 3,275,834 | 9/1966 | Stevens .............................. 356/102 |
| 3,515,885 | 6/1970 | Imadate .......................... 250/222 PC |

OTHER PUBLICATIONS

Brecht et al., "Messtechnische Erfassung von Flecken und Splittern in Halb- und Ganzstoffen mit einem Optisch-Elektronischen Gerat", *Das Papier* vol. 22, No. 10A, Oct. 1968, pp. 784-792.

*Primary Examiner*—John K. Corbin
*Assistant Examiner*—Richard A. Rosenberger
*Attorney, Agent, or Firm*—Kenway & Jenney

[57] ABSTRACT

In a method for examining pulp for shives present therein a suspension of the pulp is passed through a measuring duct with transparent walls and two mutually perpendicular light beams are directed through the measuring duct in a plane perpendicular to the direction of flow in the measuring duct. The intensities of the light beams after their passage through the measuring duct are measured by means of two photo detectors and the output signals of the photo detectors are multiplied to provide a combined signal representing the product of the output signals of the photo detectors. This combined signal is analyzed with respect to the temporary amplitude reductions occurring therein due to the presence of shives in the pulp suspension flow passing through the measuring duct. Preferably, the light beams consist of light having a wavelength within the infra-red range.

12 Claims, 2 Drawing Figures

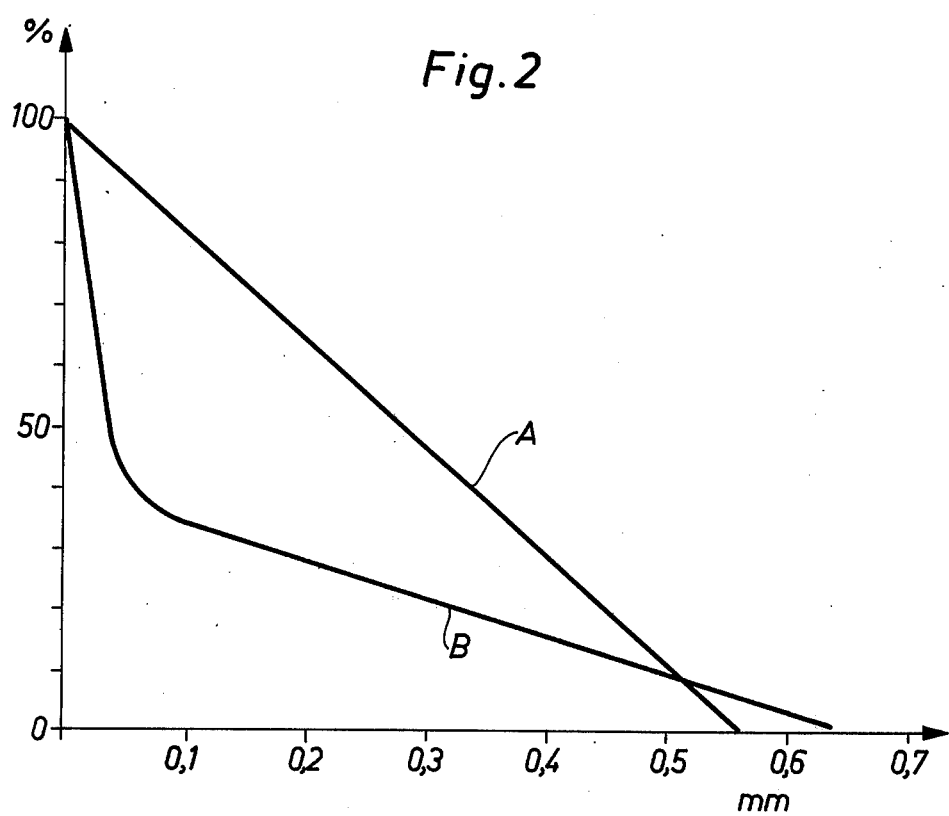

METHOD AND DEVICE FOR EXAMINING PULP FOR THE PRESENCE OF SHIVES

The present invention is related to a method and a device for testing and examining pulp for the presence of shives therein.

A "shive" is a larger fiber bundle consisting of two or more fibers which adhere to each other and which have not been completely separated from each other during the production of the pulp. The shives differ from the fibers in the pulp primarily in that they have a larger cross-section dimension than the fibers and thus generally also a somewhat larger length in average than the fibers. Whereas the fibers generally have a cross-section dimension (thickness) of 10–50 $\mu$ the shives, or what is generally called shives, have a corresponding cross-section dimension from 80–150 $\mu$ and upwards. The lower limit for the cross-section dimension of what is called shives is often dependent on the capability of the available measuring apparatus of distinguishing between thin shives, i.e. shives having a comparatively small cross-section dimension, and fibers. The average length of the shives is generally 1.5 to 2 times larger than the average length of the fibers, but this value depends on the type of the pulp.

The presence of shives in a paper pulp is an important factor for the quality of the pulp. One reason for this is that each shive will cause a weak spot or an initiative to rupture in the paper web being manufactured from the pulp and therefore increase the risk of rupture of the paper web during its manufacture. Further, a shive located in the surface of the manufactured paper will also impair the printing qualities of the paper, for instance in that the shive accepts and adsorbs the printing ink in a manner different from the surrounding paper or in that the shive comes loose from the paper surface during the printing process and possibly adheres to the printing form or printing plate. Consequently, it is of important interest to be able to examine pulp with respect to the presence of shives therein, the primary interest being to determine the total amount of shives in a given quantity of pulp but also to obtain information on the size or the size range of the shives present in the pulp.

A prior art method for examining paper pulp for the presence of shives therein comprises the steps of passing a suspension of the pulp through a measuring duct having transparent walls and directing a substantially parallel beam of light from a light source located at one side of the measuring duct through the measuring duct towards a photo detector located on the opposite side of the measuring duct in such a manner that the direction of the light beam is substantially perpendicular to the longitudinal direction of the measuring duct, i.e. to the direction of flow of the pulp suspension. A shive present in the pulp suspension will, when it passes through the light beam, give cause to a reduction in the intensity of the light received by the photo detector and thus to a corresponding reduction in the amplitude of the output signal of the photo detector. The magnitude of this reduction in intensity and amplitude, respectively, constitutes a measure of the cross-section dimension of the shives in a direction perpendicular to the light beam, whereas the duration of the reduction in intensity and amplitude, respectively, is a measure of the length of the shive, as the shives orient themselves in the pulp suspension flow with their longitudinal direction substantially coinciding with the direction of flow. By analyzing the output signal of the photo detector with respect to the amplitude variations in the signal it is consequently possible to obtain information of the presence of shives in the pulp. As the cross-section of a shive is often rectangular, i.e. the shive is thin and broad, it is the preferred practice to direct two light beams through the measuring duct at right angles to each other and in a common plane perpendicular to the longitudinal direction of the measuring duct. These two light beams are, after their passage through the measuring duct, received by two corresponding photo detectors and the output signals of these photo detectors are combined to a combined signal, which is subsequently analyzed, as mentioned above, with respect to the occurrence of amplitude variations therein caused by shives in the pulp.

It will be appreciated that in a measuring process of this type it is of fundamental importance that it is possible to distinguish between, on the one hand, the reduction of the intensity of the light beam caused by a shive passing through the light beam and, on the other hand, the reduction of the intensity of the light beam caused by the fibers in the pulp suspension flow, which are at the same time present within the light beam. Consequently, it is essential that the measuring process has a large sensitivity to shives but at the same time a low sensitivity to fibers. This can also be expressed by saying that it shall be possible to detect a shive even if at the same time a large number of fibers are present in the measuring duct illuminated by the light beams. The importance of this condition is illustrated by the fact that a typical value for the ratio between the number of fibers and the number of shives in a paper pulp is that the number of fibers is of the order $10^5$ larger than the number of shives. This value corresponds to a proportion of shives in the pulp of about 1% by weight, which is even a comparatively high value for many pulp qualities.

Prior art measuring processes of the kind described in the foregoing and prior art measuring devices operating according to these measuring processes are rather unsatisfactory in the above-discussed respect.

The object of the present invention is therefore to provide an examination method of the type described in the foregoing and a corresponding device, which provide a substantially increased sensitivity to the shives with a maintained insensitivity of fibers, i.e. a substantially increased possibility of detecting a shive passing through the light beams even if a large number of fibers are at the same time present within the light beams.

According to the invention this is achieved primarily in that the output signals from the two photo detectors are combined by multiplication so that a combined signal representing the product of the output signals of the two photo detectors is provided, this combined signal being analyzed with respect to amplitude variations occurring therein due to shives in the pulp.

The manner of combining the output signals of the two detectors which presents itself immediately and which is most obvious, is a simple addition of the signals to each other. This is also the method used in the prior art. However, it has been found that if the combined signal is instead producted by multiplication of the output signals of the two photo detectors with each other, a substantially increased ratio between the measuring sensitivity to shives and the measuring sensitivity to fibers will be obtained.

According to the invention light within the infrared wavelength range is preferably used, since it has been found that this gives an additional substantial increase in the ratio between the sensitivity to shives and the sensitivity to fibers as compared to the result obtained when using visible light.

In the following the invention will be further described in more detail with reference to the accompanying drawings, in which FIG. 1 shows schematically a device for examining pulp with respect to shives present therein, in which the invention is employed; and FIG. 2 is a graphical presentation of the transmission of a light beam passing through the measuring duct as a function of the cross-section dimension of a shive affecting the light beam; on the one hand when using a beam of a visible light and on the other hand when using a beam of infra-red light.

FIG. 1 shows very schematically and only in principle a device for examining pulp for the presence of shives therein, comprising a measuring duct 1 with transparent walls, through which a flow of a suspension of the pulp to be examined is passed, as indicated by an arrow 2. From light sources with associated optical systems (not shown in the drawings) two mutually perpendicular light beams 3 and 4 are directed through the measuring duct 1 in a common plane perpendicular to the longitudinal direction of the measuring duct 1. Each of these light beams 3 and 4 consists of substantially parallel light rays and is shaped by the optical system associated with the light source so as to have a comparetively thin rectangular cross section so that the light beam has substantially the form of a thin ribbon disposed in the plane perpendicular to the longitudinal axis of the measuring duct 1. After their passage through the measuring duct 1 the two light beams 3 and 4 are received by photo detectors 5 and 6, respectively, which consequently will provide output signals proportional to the intensities of the light beams 3 and 4, respectively, after their passage through the measuring duct 1 and the flow of pulp suspension present in the measuring duct. It will be appreciated that if a shive is present in the pulp suspension, this shive will, when passing through the light beams 3 and 4, "cast a shadow" on each of the photo detectors 5 and 6 so that the light intensities received by these photo detectors are reduced. It will also be appreciated that the magnitude of this reduction in intensity and thus the magnitude of the corresponding amplitude reduction in the output signals of the photo detectors is a measure of the breadth or width of the shive in the directions perpendicular to the light beam 3 and the light beam 4, respectively, i.e. in two mutual perpendicular directions. Consequently, in this way the "breadth" as well as the "thickness" of the shive are measured, as the shive tends to orient itself in the pulp suspension flow in the measuring duct 1 with its longitudinal direction coinciding with the flow direction. It will also be appreciated that the duration of the intensity reduction and thus the duration of the amplitude reduction in the output signals of the two photo detectors 5 and 6 will be a measure of the length of the shive.

The output signals from the two photo detectors 5 and 6 are supplied to a signal multiplier 8 which provides an output signal corresponding to the product of the signals from the photo detectors 5 and 6. It will be appreciated that also the output signal from the signal multiplier 8 will display a temporary amplitude reduction when a shive in the pulp suspension flow in the measuring duct 1 passes through the two light beams 3 and 4. The magnitude of this temporary amplitude reduction will be a measure of the cross-section area of the shive, whereas the duration of the amplitude reduction will be a measure of the length of the shive. The output signal from the signal multiplier 8 is supplied to a signal analyzing and displaying unit 7, in which the signal is analyzed with respect to the temporary amplitude reductions occurring therein due to shives in the pulp suspension flow, as will be described more in detail in the following.

By multiplying the output signals from the two photo detectors 5 and 6 and analyzing a combined signal corresponding to the product of the two output signals from the photo detectors the possibility of detecting shives in the pulp suspension flow, in spite of the fact that pulp suspension flow contains at the same time also fibers affecting the light beams 3 and 4, becomes much larger than if the output signals of the photo detectors 5 and 6 were combined by simple addition of the signals to each other.

A further substantial improvement in this respect is achieved, when according to a preferred embodiment of the invention light within the infra-red wavelength range is used instead of visible light. The reason for this is probably that it has been found that the relation between the reduction in the intensity of the light beam caused by a shive and the thickness of the shive is a substantially linear function when using visible light but, on the contrary, a non-linear function when using infra-red light. This phenomenon is illustrated graphically in FIG. 2, which shows the relation between the transmission of a light beam, i.e. the percentage ratio between the exit intensity of the light beam leaving the measuring duct and the incident intensity of the light beam directed towards the measuring duct, as a function of the thickness of a shive in the measuring duct affecting a light beam; the curve A illustrating this relation when using visible light, or more exactly light from a halogene lamp, and the curve B illustrating the relation obtained when using infra-red light, or more exactly light from a luminiscence diode having the wavelength 930 nm. As immediately obvious from a comparison between the two curves A and B, the use of infrared light (the curve B) provides a much stronger influence upon the transmission of the light beam from shives having a thickness from about 80 $\mu$ and upwards as compared to the influence upon the transmission caused by fibers which have a cross-section dimension of the order of 10–50 $\mu$, than the case is when using visible light (the curve A).

Experiments and calculations have been made for determining the maximum number of fibers that can be permitted to affect the two light beams 3 and 4, if it shall be possible at the same time to detect a shive. This has been made for four different cases: (1) visible light and addition of the output signals of the photo detectors, (2) visible light and multiplication of the output signals of the photo detectors, (3) infra-red light and addition of the output signals of the photo detectors, and (4) infrared light and multiplication of the output signals of the photo detectors. These experiments and calculations gave the values given in the following table for the maximum number of fibers than can be permitted to affect the two light beams without making it impossible to detect a shive at the same time. The experiments and the calculations were made for two different shive thicknesses; on the one hand 100 μ and on the other hand 200 μ.

| Shive thickness μm | Added signals | | Multiplied signals | |
|---|---|---|---|---|
| | Visible light | IR-light | Visible light | IR-light |
| 100 | 3 | 6 | 8 | 40 |
| 200 | 5 | 7 | 20 | 50 |

As immediately obvious from this table, multiplication of the output signals of the photo detectors instead of an addition of the signals to each other as well as the use of infra-red light instead of visible light produces a pronounced improvement of the sensitivity to shives relative to fibers. However, by far the best result is obtained, if both multiplication of the output signals of the two photo detectors and infra-red light is used simultaneously, in which case a sensitivity to shives relative to fibers is obtained, which is about 10 times larger than when using addition of the output signals of the photo detectors and visible light.

In the most simple embodiment of the invention the analyzer unit 7 can be designed to count the number of temporary amplitude reductions in the output signal from the signal multiplier 8 over a given period of time, which temporary amplitude reductions are caused by shives in the pulp suspension flow. This gives information of the number of shives in the quantity of pulp which has passed through the measuring duct 1 during the said period of time.

According to a preferred embodiment of the invention the signal analyzer unit 7 is designed to determine also the magnitude and the duration of said temporary amplitude reductions in the output signal of the signal multiplier 8, which are caused by shives. This gives information on the cross-section dimension (thickness) and the length of the shives, since as mentioned in the foregoing the magnitude of the amplitude reduction is a measure of the cross-section dimension of the shive causing the amplitude reduction, whereas the duration of the amplitude reduction is a measure of the length of the shive. Preferably the analyzer unit may then be designed to grade the amplitude reductions in the output signals of the signal multiplier 8 into classes with respect to their magnitude and duration and to count the total number of amplitude reductions in each such class over a given period of time. This gives information on the total number of shives in the pulp within a number of size classes of shives. As an example the shives may be classed in 16 thickness/length classes having for instance the thickness ranges 80-150 μ, 150-250 μ, 250-500 μ and >500 μ and the length ranges 0-1 mm, 1-2 mm, 2-4 mm, and >4 mm.

I claim :

1. A method of examining pulp for the presence of shives therein, comprising the steps of passing a suspension of the pulp through a measuring duct with transparent walls, directing two mutually perpendicular beams of light through the measuring duct in a common plane perpendicular to the direction of the flow in the measuring duct, measuring the intensities of said two light beams after their passage through the measuring duct by means of two photo detectors, multiplying the output signals of said two photo detectors so as to provide a combined signal representing the product of the output signals of the photo detectors, and analyzing this combined signal with respect to amplitude variations ocurring therein.

2. A method as claimed in claim 1, wherein light having a wavelength within the infra-red range is used for said two light beams.

3. A method as claimed in claim 1, wherein the number of temporary amplitude reductions in said combined signal caused by shives in the pulp suspension flow is counted over a given period of time.

4. A method as claimed in claim 1, wherein the magnitude of the temporary amplitude reductions in the combined signal caused by shives in the pulp suspension flow is measured.

5. A method as claimed in claim 1, wherein the duration of the temporary amplitude reductions in the combined signal caused by shives in the pulp suspension flow is measured.

6. A method as claimed in claim 1, wherein the temporary amplitude reductions in the combined signal caused by shives in the pulp suspension flow are divided into classes with respect to their magnitude and/or duration and that the number of amplitude reductions within each such class is counted over a given period of time.

7. A device for examining pulp with respect to the presence of shives therein, comprising a measuring duct with transparent walls, two light sources arranged outside said measuring duct for directing two, mutually perpendicular light beams through the measuring duct in a common plane perpendicular to the direction of flow in the measuring duct, two photo detectors arranged to receive said two light beams, respectively, after their passage through the measuring duct and for producing output signals representing the intensity of said light beams, signal multiplying means for receiving the output signals of said two photo detectors and producing a combined signal representing the product of the output signals of the photo detectors, and signal analyzing means for receiving said combined signal from said signal multiplying means and for analyzing this signal with respect to amplitude variations occurring therein.

8. A device as claimed in claim 7, wherein said light sources are of a type emitting radiation within the infra-red wavelength range.

9. A device as claimed in claim 7, wherein said signal analyzing means are arranged to count the number of temporary amplitude reductions occurring in said combined signal over a given period of time.

10. A device as claimed in claim 7, wherein said signal analyzing means are arranged to determine the magnitude of the temporary amplitude reductions occurring in said combined signal.

11. A device as claimed in claim 7, wherein said signal analyzing means are arranged to determine the duration of the temporary amplitude reductions occurring in said combined signal.

12. A device as claimed in claim 7, wherein said signal analyzing means are arranged to classify the temporary ampltitude reductions occurring in said combined signal in classes with respect to their magnitude and/or duration and to count the number of amplitude reductions within each such class over a given period of time.

* * * * *